United States Patent [19]

Mescher

[11] Patent Number: 5,045,320

[45] Date of Patent: Sep. 3, 1991

[54] LARGE MULTIVALENT IMMUNOGEN

[75] Inventor: Matthew F. Mescher, Del Mar, Calif.

[73] Assignee: Medical Biology Institute, LaJolla, Calif.

[21] Appl. No.: 327,822

[22] Filed: Mar. 23, 1989

[51] Int. Cl.$^5$ .................. A61K 39/385; A61K 37/66; A61K 9/127

[52] U.S. Cl. ........................................ 424/450; 424/9; 424/85.1; 424/85.2; 424/85.4; 424/88; 436/527

[58] Field of Search .................... 424/85.1, 88, 450, 9, 424/85.2, 85.4; 436/527

[56] References Cited

U.S. PATENT DOCUMENTS 4,861,589 8/1989 Ju ............................................ 424/93

OTHER PUBLICATIONS

Goldstein et al. (1987), J. Immunol. 138:2034–2043.
Goldstein et al. (1986), J. Immunol. 137:3383–3392.
Goldstein et al. (1988), J. Immunol. 140 (11):3707–11.

Primary Examiner—Jeffrey E. Russel
Assistant Examiner—Kay K. Kim
Attorney, Agent, or Firm—Grant L. Hubbard

[57] ABSTRACT

Immunization and/or therapeutic in vivo introduction of ligands bound alone or in combination with other molecules, arrayed on solid supports having greater then about $0.2\mu$ diameter to elicit and augment in vivo T cell mediated responses are described.

18 Claims, 4 Drawing Sheets

LARGE MULTIVALENT IMMUNOGEN

GOVERNMENT RIGHTS

The research from which this invention arose was supported by the United States Government under NIH grant ROu CA43062 and the Government has certain rights to and under the invention and this patent.

BACKGROUND OF THE INVENTION

This invention relates to immunology, and, more specifically to novel in vivo immunization/or therapeutic methods wherein ligands bound by T cell receptor complex, alone or in combination with other molecules, arrayed on solid supports having greater than about 0.2μ diameter which are known to elicit and augment in vivo T cell medicated responses.

For the convenience of the reader, the following abbreviations which are used in describing the background of the invention and the invention are defined as follows:

Definitions

Class I protein: Products of the K, D or L loci of the murine MHC, for example $H-2K^k$ or $H-2^b$. (H-2 protein is the same as class I protein.)
ConA: Concanavalin A (extract of jack beans, Canavalia ensiformis, a mitogenic lectin).
CTL: Cytolytic T lymphocytes.
DMSO: Dimethyl sulfoxide.
E: Effector cells.
EL4: A murine thymoma.
I.p.: Intraperitoneal.
I.v.: Intravenous.
LMI: Large multivalent immunogen (referred to in earlier publications as "pseudocytes").
MHC: Major histocompatibility complex.
P815: A murine mastocytoma.
PBL: Peripheral blood lymphocytes.
PBS: Phosphate buffered saline.
pCTL: Precursor cytolytic T lymphocytes.
PEL: Peritoneal exudate lymphocytes.
RDM4: A murine lymphoma.
S.c.: Subcutaneous.
T: Target cells.
TCR: T cell receptor.
TH: T helper cells.

Activation of helper and cytotoxic T cells plays a critical role in eliciting in vivo immune responses, both humoral and cell mediated, against foreign antigens; foreign antigens being components of bacteria, parasites, viruses, transformed cells or transplanted cells. Immunization with vaccines containing foreign antigens is effective in eliciting humoral (antibody) responses, but generally ineffective in activation of cell mediated immunity. Thus, current formulations are ineffective in activation of a major arm of immune system defense against invasion by foreign organisms.

T cells are normally activated as a result of binding to antigen displayed on the surface of another cell; the binding and activation being mediated by the antigen-specific, major histocompatibility complex (MHC)-restricted T cell receptor (TCR). In vitro studies have demonstrated that MHC molecules alone, or together with foreign antigen, can activate T cells when incorporated onto artificial membranes. (Burakoff, S. J. and M. F. Mescher 1982. Reconstituted membranes and liposomes in the study of lymphocyte interactions. In: Poste, G., Nicholson, B., eds. Cell Surface Reviews. North Holland, Elsevier. Goldstein, S. A. N., and M. F. Mescher 1986). Cell-sized, supported artificial membranes (pseudocytes): Response of precursor cytotoxic T lymphocytes to class I MHC proteins. J. Immunol. 137:3383.) These in vitro studies have also suggested that the area of surface interaction possible between the T cell and antigen-bearing membrane as well as the surface density of antigen, are important in efficient activation. (Goldstein, S. A. N., and M. F. Mescher 1987. Cytotoxic T cell activation by class I protein on cell-size artificial membranes: antigen density and Lyt-$\frac{2}{3}$ function. J. Immunol. 138:2034. Herrmann, S. H. and M. F. Mescher 1986.) The requirements for antigen multivalency in Class I antigen recognition and triggering of primed precursor cytolytic T lymphocytes. (J. Immunol. 136:2816.) Although in vitro stimulation can occur, effective use of subcellular forms of known T cell antigens for in vivo elicitation or augmentation of cytotoxic T cell responses have not been reported.

Development of immunogens for use in vivo as vaccines or therapeutic agents has been a subject of intense interest for a very long time, and numerous formulations have been tested in animal models and in humans. While many are very effective at eliciting humoral response, most are ineffective in activating cell mediated immunity. Most formulations do not meet the critical requirements for pCTL activation demonstrated by in vivo experiments reported here. The importance of multivalency in producing an effective immunogen has been appreciated to some extent. Recent examples include iscom's (immunostimulating complex), particles consisting of amphipathic antigens and a hydrophobic matrix (Quil A) with adjuvant properties (Morein, B. 1988. The iscom antigen-presenting system. Nature 332:287), and proteosomes, having antigen in a liposome-like physical state (Lowell, G. H., L. F. Smith, R. D. Seid and W. D. Zollinger 1988). Peptides bound to proteosomes via hydrophobic feet become highly immunogenic without adjuvants. (J. Exp. Med. 167:658.) Although multivalent, these are still small relative to cells, iscoms having a diameter of about 0.035 μ and proteosomes a diameter of about 0.1μ. Thus, they may optimize uptake by macrophages of interaction with B cells, but are well below the critical size for activation of pCTL. Furthermore, currently formulated immunogens do not bear the class I MHC proteins involved in recognition by H-2-restricted CTL.

Considerable research effort has focused on studies of the cell surface molecular requirements for antigen-specific in vitro activation of precursor (pCTL) and effector cytolytic T lymphocytes (eCTL). A major approach to this has been use of well-defined artificial membranes bearing the relevant affinity-purified antigens. Novel methods have been developed for preparing artificial membranes supported on cell-sized (>0.2μ, e.g. 5μ diameter) beads and it has now been discovered, as disclosed here, that these artificial membranes produce in vivo immunogenic responses which do not result from the injection of small immunogens. These supported membranes, which were referred to as pseudocytes in our previous publications, are termed Large Multivalent Immunogens (LMI).

SUMMARY OF THE INVENTION

The invention features production of Large Multivalent Immunogen (LMI)—ligands in a stable array on a physical support of greater than 0.2 micron (in diameter or in longest dimension)—and their introduction in vivo for prophylactic or therapeutic purposes. Ligands include: i) molecules which are bound by surface receptors, including T cell receptors, in an antigen specific manner; and ii) molecules which interact with cell surface components in a non-antigen-specific manner to promote antigen-specific interactions or cell activation. LMI production is by any of a variety of methods which result in a stable surface array, including incorporation into a membrane or adsorption or covalent coupling to a surface, the critical parameter being the size of the physical support.

Based on in vivo results, experiments have been done to explore the in vivo effects of administering cell-size, antigen-bearing artificial membranes, termed Large Multivalent Immunogens (LMI). LMI bearing alloantigen do not stimulate generation of a CTL response when administered i.p. They do, however, dramatically augment an alloantigen-specific response when administered along with allogeneic tumor cells. Similar results have been obtained in examining lytic responses to tumor cells growing in syngeneic animals. I.p. inoculation of EL4, RDM4 or P815 tumor cells into syngeneic mice results in tumor growth and ultimately death of the mice. If LMI bearing tumor antigen, in the form of plasma membrane isolated from the tumor cells, are administered at the time of inoculation, a strong lytic response develops within 10 to 12 days. Moreover, the peritoneal tumor load in LMI-treated animals is dramatically reduced (or eliminated; >99% reduction) in comparison to controls.

The invention is embodied in a method of treating a mammal having a tumor to activate cell responses. The method is carried out by the in vivo administration of Large Multivalent Immunogen consisting essentially of multivalent ligand arrays supported on large particles having a major dimension greater than 0.2 micron. In a preferred method, the Large Multivalent Immunogen has a diameter of about $5.0\mu$. The Large Multivalent Immunogen may have a much larger diameter; however, no significant advantages for larger diameters are known. The cell activation may constitute the activation of antigen-specific T cells, macrophages, monocytes or natural killer cells.

The invention is embodied in a method of treating a mammal which is not known or suspected of having a tumor to activate cell responses and thus inhibit or prevent the growth of tumors in the mammal. The method is carried out by the in vivo administration of large multivalent immunogen consisting essentially of multivalent ligand arrays supported on large particles having a major dimension greater than 0.2 micron. In a preferred method, the large multivalent immunogen has a diameter of about $5.0\mu$. The cell activation may constitute the activation of antigen-specific T cells, macrophages, monocytes or natural killer cells.

Individual T cells differ with respect to the specificity of their antigen-specific receptor (TCR), but otherwise display common activation requirements. Data demonstrating in vivo efficacy of LMI for allogeneic (transplantation) and tumor models is presented. Implicit in these findings is application of LMI to immunization or treatment of other diseases involving T cell responses including viral, bacterial, parasitic, graft-versus-host, and autoimmune diseases. In all cases the essential method is the same, and use would differ only with respect to the choice of antigen (ligand) to be incorporated onto the LMI.

Either for the treatment of prevention of mammalian disease, the method may be carried out with a composition of matter as described above with or without the addition of a ligand in a physical form different than that of the large multivalent immunogen. The ligand component may consist essentially of antibodies specific for a cell surface, an antigen, a hapten, or another immunogenic species, or a mixture of various ligands. The term "ligand" is used here in the general immunochemical sense of the term, i.e. any molecule that forms a complex with another molecule, or binds to or includes a specific determinant, such as on a cell, surface or molecule, the more common examples of which are antibodies and antigens. (See, e.g., Stites, D. P., Stobo, J. D. and Wells, J. V. BASIC & CLINICAL IMMUNOLOGY, Appleton & Lange, Norwalk, Conn., 1987.)

BRIEF DESCRIPTION OF THE DRAWINGS

CD2F1 mice were injected i.p. with the indicated stimulus. Tumor cells and beads were used at $10^7$ beads. $H-2K^b$ was purified from EL4 tumor cells and $H-2K^k$ from RDM4 tumor cells. Ten days after injection, peritoneal cells were removed and assayed for cytolytic activity using $^{51}Cr$-labeled RDM4 and EL4 targets in a four-hour assay at the indicated effector:target ratios. Results are shown as % specific chromium release. Cells from mice which received RDM4 stimulus (alone or with beads) did not kill EL4 targets, and cells which received EL4 stimulus (alone or with beads) did not kill RDM4 targets (not shown on graph).

C57BL/6 mice were injected i.p. with the stimulus indicated. RDM4 tumor cells and LMI were used at $10^7$ per animal. LMI bearing a high density of antigen were made using 10 $\mu$g H-2 per $10^7$ beads and low density LMI were made using 3 $\mu$g per $10^7$, $H-2K^k$ antigen was purified from RDM4 cells and $H-2^d$ antigen from P815 tumor cells. Ten days after injection, peritoneal cells were removed and assayed for cytolytic activity using $^{51}Cr$-labeled RDM4 ($H-2^k$) and P815 ($H-2^d$) targets. PEL from 2 mice/group were pooled for assay.

Treated mice (+) received $10^7$ LMI bearing tumor antigen (plasma membrane) at the same time. Nine (EL4 and RDM4) or eleven (P815) days later peritoneal cells were harvested and counted. Values shown are averages obtained for two mice in each group. Percent reduction of tumor load in treated animals compared to untreated (−) controls is shown.

C57BL/6 mice were inoculated i.p. with $10^6$ live EL4 cells. Administered at the same time were $10^7$ LMI bearing EL4 plasma membrane, or EL4 plasma membrane in suspension. Membranes were used at an amount equivalent to that on the LMI (1x plasma membrane) or at a 10-fold higher dose (10x plasma membrane). Peritoneal cells were harvested and counted on day 13. Values are averages obtained for two mice in each group, and the range obtained for the pair is shown.

CD2F1 mice were inoculated i.p. with $10^5$ P815 cells. At the same time, LMI having either P815 plasma membrane or normal mouse serum protein (NMS) were administered by the indicated route, using $10^7$ LMI/mouse in all cases. Peritoneal cells were harvested and counted eleven days after inoculation. Groups treated with tumorantigen bearing LMI consisted of four mice each and values shown are averages with standard deviations indicated. Control groups (tumor only and NMS-LMI treated) were of two mice each and averages are shown. Recovery of peritoneal washout cells from normal mice which received neither tumor inoculum or LMI was determined for six mice (bottom bar), and the standard deviation is indicated.

Tumor-specific cytolytic activity of peritoneal exudate lymphocytes from mice treated with LMI, C57BL/6 mice were inoculated with $10^6$ live EL4 cells. Treated mice received $10^7$ LMI bearing EL4 membrane at the same time (EL4+LMI). Control mice without live tumor were also injected with $10^7$ LMI bearing EL4 membrane (LMI only). After 12 days, peritoneal cells were harvested, allowed to adhere to plastic for one hour and the non-adherent cells assayed for lytic activity in a 4-hour Cr-release assay using EL4 and RDM4 targets. LMI treated mice were the same as those shown in FIG. 4 where the tumor load had been reduced >99% by LMI treatment. Cells from individual mice were assayed and results shown for both animals in each group. Killing is expressed as % specific release. Spontaneous release was 195 cpm for EL4 and 248 cpm and total releasable was 2549 for EL4 and 2938 for RDM4.

In obtaining the data graphically depicted in FIG. 7-A, C57BL/6 mice were inoculated i.p. with $10^6$ live EL4 cells and $10^7$ LMI bearing EL4 antigen administered at the same time. Twelve days later spleens (2 mice) were removed, pooled and placed into culture with or without irradiated EL4 cells. After 6 days of in vitro culture, cells were assayed for lytic activity in a 4-hour Cr-release assay using EL4 and RDM4 targets. Results are shown for cells cultured with irradiated EL4. Cells cultured in the absence of stimulators had no lytic activity on either target.

In obtaining the data graphically shown in FIG. 7-B, CD2F1 mice were inoculated with $10^6$ live P815 cells and treated at the same time with either nothing (None), $10^7$ LMI bearing P815 antigen (LMI-P815), or $10^7$ LMI bearing normal mouse serum (LMI-NMS). Seven days later, spleens were removed (2 mice per group) and placed into culture alone or with irradiated P815 cells. After 6 days of in vitro culture, lytic activity was assayed on P815 and RDM4 targets. Results obtained for restimulated cells on P815 targets are shown. No killing of RDM4 targets was found. Cells which were not restimulated in vitro lysed neither P815 nor RDM4 targets.

DESCRIPTION OF THE PREFERRED EMBODIMENTS

A central finding of in vitro studies is that CTL binding and transmembrane signalling require a highly multivalent interaction over an appreciable area of the CTL surface. LMI satisfy these critical requirements, and are quantitatively as effective as antigen-bearing cells in stimulating in vitro responses. The in vivo effects of antigen-bearing LMI have been defined in experiments examining allogeneic responses, and the potential applications of LMI in immunotherapy have been evaluated using three murine tumor model systems.

LMI-bearing affinity-purified alloantigen do not stimulate generation of a CTL response when administered i.p., but the in vivo response to irradiated allogeneic cells is greatly augmented (10 to 50-fold) when LMI are also administered. This unexpected and dramatic augmentation is antigen-specific and dependent on the alloantigen density on the LMI.

CTL responses to syngeneic tumors, using LMI-bearing purified plasma membranes isolated from the tumor cells have been examined. Tumor cells examined have included P815 (a mastocytoma), EL4 (a thymoma) and RDM4 (a lymphoma). All grow rapidly in the peritoneums of syngeneic mice and kill the mice within two to four weeks. In vivo administration of LMI bearing tumor membranes results in a dramatic reduction in the peritoneal tumor load, greater than 99% reduction compared to controls on day 12 in some cases. As in the case of allogeneic response, LMI bearing tumor antigen do not elicit a CTL response when administered alone. However, peritoneal lymphocytes from animals inoculated with tumor and treated with LMI develop a high level of tumor-specific cytolytic activity. Furthermore, spleen cells from animals whose tumor load has been reduced or eliminated by LMI treatment mount a strong, tumor-specific response when restimulated in vitro, while spleen cells from untreated, tumor-bearing animals show little if any response. Thus, administration of tumor antigen in the appropriate form can dramatically reduce tumor growth. The effect appears very likely to be mediated, at least in part, by tumor-specific CTL.

The application of these discoveries and methods to animal and human cancer immunotherapy is immediately apparent, and application to other diseases is clearly within the skill of the art, inasmuch as the immunochemical foundation upon which this invention rests is general and not unique to tumors and the like.

The invention comprehends methods of treating a mammal to prevent or treat viral, bacterial, parasitic, graft-versus-host and autoimmune diseases, as well as the specific classes of diseases discussed above, in the mammal to activate cell responses comprising the in vivo administration of a large multivalent immunogen composition consisting essentially of multivalent ligand arrays supported on large particles having a major dimension greater than 0.2 micron, preferably using compositions wherein the large multivalent immunogen has a major diameter of about 5 microns or larger and may, optionally, include a ligand in a physical form different than that of the large multivalent immunogen and is in the form of an injectable solution.

MATERIALS AND PROCEDURES

MHC class I and class II antigens were purified by affinity chromatography. The proteins in deoxycholate-containing buffer were mixed with a suspension of SPHERISORB® ODS1 (5 micron) beads (Phase Sep, Norwalk, Conn.) and lipid added. SPHERISORB® ODS1 beads are microporous silica spherical particles having a pore size of about 80Å. C18 alkyl chains are covalently bonded to the silica. SPHEROSORB® ODS1 are manufactured and sold as column packing material for reverse-phase high pressure liquid chromatography and are generally available from chemical supply houses. A typical ratio of components used was 6 μg H-2 protein:5 nmole lipid:$10^7$ beads. The suspension was then dialyzed for 48 hr to remove deoxycholate. At the end of this time, all of the protein and lipid are associated with the beads, and about 50% of the protein is exposed at the bead surface (Goldstein, S. A. N. and M. F. Mescher 1986. Cell-sized, supported artificial membranes (pseudocytes): response of precursor cytotoxic T lymphocytes to class I. J. Immunol. 137:3383. Following dialysis, beads are prepared for use by washing several times in the appropriate buffer, with the beads being pelleted by low speed centrifugation.

Antibodies specific for components of the CTL surface were incorporated onto beads by a dilution procedure. SPHERISORB® ODS1 (5 micron) beads (Phase Sep, Norwalk, Conn.) were suspended in dimethylsulfoxide (typically 1.5 mg dry beads in 0.02 ml dimethylsulfoxide). This suspension was then added to a solution of the antibody under conditions which resulted in a large dilution of the dimethylsulfoxide. The protein-bead suspension was then agitated for 1 hour at four degrees and the beads then harvested and washed three times with buffer.

Plasma membranes isolated from tumor cells bear tumor-specific antigens. Isolated plasma membranes were coated onto SPHERISORB® ODS1 beads in the same manner as described above. Beads suspended in dimethylsulfoxide were added to a suspension of tumor cell plasma membrane in phosphate-buffered saline, allowed to incubate 1 hr at 4°, and the beads then washed twice by low speed centrifugation to remove unbound membrane vesicles.

In vitro CTL activation was assessed in one of two ways. In the first, induction of a cytolytic response by mouse spleen cells in culture was measured. Detailed procedures for this have been published. (Burakoff, S. J. and M. F. Mescher 1982. Reconstituted membranes and liposomes in the study of lymphocyte interactions. In: Poste, G., Nicholson, B., eds. Cell Surface Reviews. North Holland, Elsevier. Goldstein, S. A. N. and M. F. Mescher 1986. Cell-sized supported artificial membranes (pseudocytes): Response of precursor cytotoxic T lymphocytes to class I MHC proteins. J. Immunol. 137,3383). In the second, cloned effector CTL activation was determined by measuring their stimulated release of serine esterase activity into the medium. (Pasternak, M., C. R. Verret, M. A. Liu and H. N. Eisen 1986. Serine esterase in cytolytic T lymphocytes. Nature 322:740.)

C57BL/6 and (CBA×DBA/2)F1 (CD2F1) mice were purchased from Jackson Laboratories, Bar Harbor, MA. H-2$K^k$, H-2$K^b$ and K-$2^d$ class I murine MHC antigens were purified as previously described. (Mescher, M. F., K. C. Stallcup, C. P. Sullivan, A. P. Turkewitz and S. H. Herrmann 1983. Purification of murine MHC antigens by monoclonal antibody affinity chromatography. In: Langone, J. J., VanVunakis, H., eds. Methods in Enzymology. New York: Academic Press. 92:86.) The antigens were incorporated onto 5 micron beads using the dialysis procedure described above. The resulting LMI were suspended in phosphate-buffered saline and injected i.p. into mice at $10^7$ beads/mouse either alone or along with $10^7$ allogeneic tumor cells. Tumor cell lines used were RDM4 (H-$2^k$), a lymphoma which originated in AKR mice, and EL-4 (H-$2^b$), a thymoma of C57BL/6 origin. Ten days after injection, mice were sacrificed and peritoneal cells harvested, washed and counted. In some cases, adherent cells were removed by one cycle of adherence to plastic dishes. Cytolytic activity of the peritoneal cell population was assessed by measuring their ability to kill allogeneic tumor cell target, using $^{51}$Cr-labeled target cells in a standard 4 hr chromium release assay at several different effector (E) to target (T) ratios. Results are expressed as either % specific lysis at varying E:T ratios, or as lytic units. One lytic unit is defined as the number of effector (peritoneal) cells required to lyse 50% of the targets in the 4 hr assay.

RESULTS AND DISCUSSION

Results of in vivo experiments using two mouse models have demonstrated the ability of LMI to induce cell-mediated responses and reduce tumor growth. The critical findings are summarized and discussed here, and details of the data and control experiments are provided in the following section.

The first model employed is that of allogeneic CTL induction, in which CTL specific for Class I MHC antigens on a foreign cell are activated. Introduction of an allogeneic tumor into an animal results in induction of a specific CTL response and rejection of the tumor. Previous attempts in our laboratory to use antigen on liposomes to induce this response in vivo resulted in generation of humoral (antibody) response but no evidence could be obtained for induction of cellmediated immunity despite the fact that this form of antigen can induce in vitro CTL response. Liposomes are particulate and provide a multivalent form of antigen, but are small, having a diameter of less than 0.1 micron.

In vivo administration of MHC antigen on LMI results in a dramatic augmentation of an allogeneic CTL response, when administered along with live tumor cells.

TABLE I

| Stimulus | Lytic Units (total) Target | |
|---|---|---|
| | RDM4 | EL4 |
| EL4 | 1 | 19 |
| RDM4 | 6 | 1 |
| Kk LMI | 0 | 0 |
| EL4 + Kk LMI | 0 | 26 |
| RDM4 + Kk LMI | 625 | 8 |

Alloantigen on LMI specifically augment in vivo activation of CTL response to alloantigen-bearing tumor cells. Tumor cells and/or LMI were injected i.p. into CD2F1 mice. Cells and LMI were used at $10^7$ per animal. LMI were prepared using 10 μg H-2$K^k$ per $10^7$ beads. Ten days after injection, peritoneal cells were removed and assayed for cytolytic activity using chromium labeled RDM4 and EL4 target cells at three E:T ratios. Cytolytic activity is shown as lytic units, calculated as described in Methods.

As shown in Table I, RDM4 (H-$2^k$) cells stimulated a response of 6 lytic units. LMI bearing H-$2K^k$ stimulated no response when administered alone, but when administered along with tumor cells augmented the response about 100-fold to 625 lytic units. This augmented response remained specific, in that the effector cells effectively killed targets bearing the H-$2^k$ antigen but had little killing activity for EL-4 (H-$2^b$) targets bearing a different antigen.

Figure 1A:
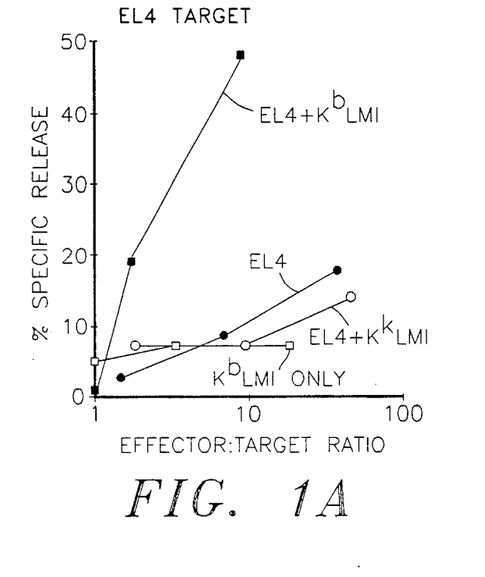
FIG. 1 graphically depicts data showing that the augmentation of in vivo CTL response is specific for the antigen on the LMI surface.
Figure 1B:
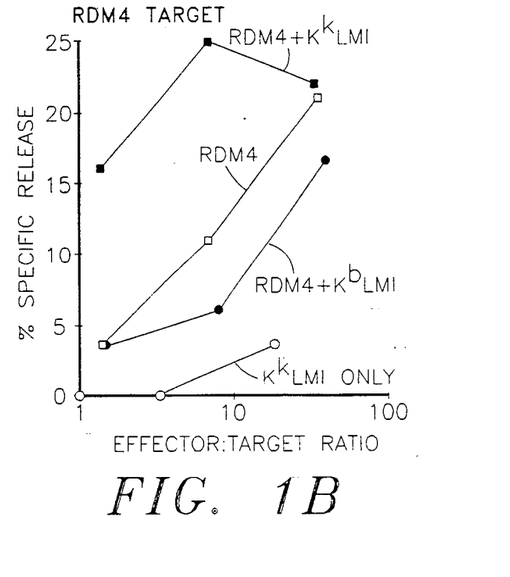
Figure 2A:
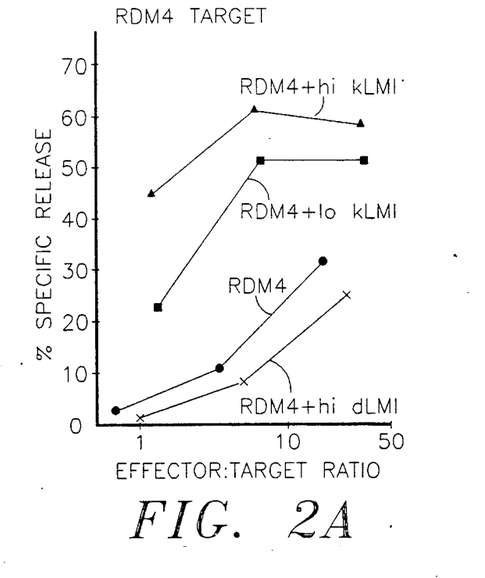
FIG. 2 graphically depicts data showing that the specific augmentation of in vivo CTL activation depends on the antigen density on the LMI surface.
Figure 2B:
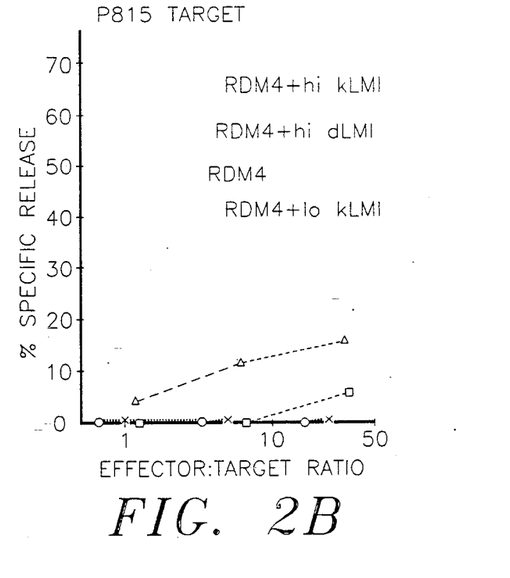

Additional experiments have consistently yielded 20 to 100-fold augmentation with LMI treatment and further confirmed the antigen specificity of the effect (FIG. 1). The efficiency of augmentation depends on the surface density of antigen on the LMI (FIG. 2). Augmentation also depends on the size of the antigen-bearing particle; injection of the same purified antigen on liposomes ($<0.2\mu$ diameter) did not augment responses.

Augmentation of the induction of allogeneic cytolytic activity by LMI indicated the potential of using LMI to augment protective CTL responses and thus provide therapy for a variety of diseases including viral infections and cancer. Augmentation of a weak cytolytic response by LMI bearing the appropriate antigen could result in production of a CTL population able to effectively eliminate the virally infected or cancerous cells causing disease.

Figure 3:
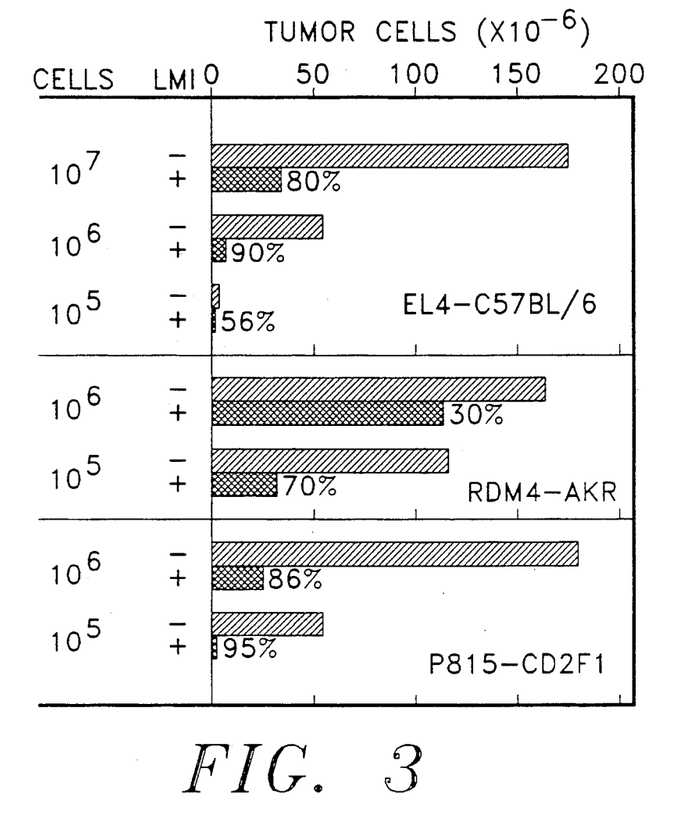
FIG. 3 graphically depicts data showing that administration of LMI reduces peritoneal tumor load.

In order to test this, three different murine tumor models have been examined. LMI were prepared by coating beads with plasma membrane vesicles isolated from RDM4, P815 and from EL4 tumor cells. RDM4 is a lymphoma which originated in AKR mice, P815 a mastocytoma which originated in DBA2 mice, and EL4 a thymoma of C57BL/6 origin. The tumors, when injected i.p. into syngeneic mice (i.e. of the strain of origin), grow rapidly and kill the mice within 10 to 20 days. Plasma membranes were purified from the tumor cells and used as antigen, with the membrane vesicles incorporated onto LMI using the procedure involving dilution from dimethylsulfoxide. For all three tumors, administration of LMI bearing the appropriate antigen resulted in a dramatic reduction in the number of tumor cells present 9 days after inoculation (FIG. 3). This dramatic reduction in tumor load has been reproducibly observed in numerous experiments, and in many cases the number of cells recovered from LMI-treated animals is no different than the number recovered from control animals which never received tumor; i.e. LMI treatment may have completely eliminated tumor.

Figure 4:
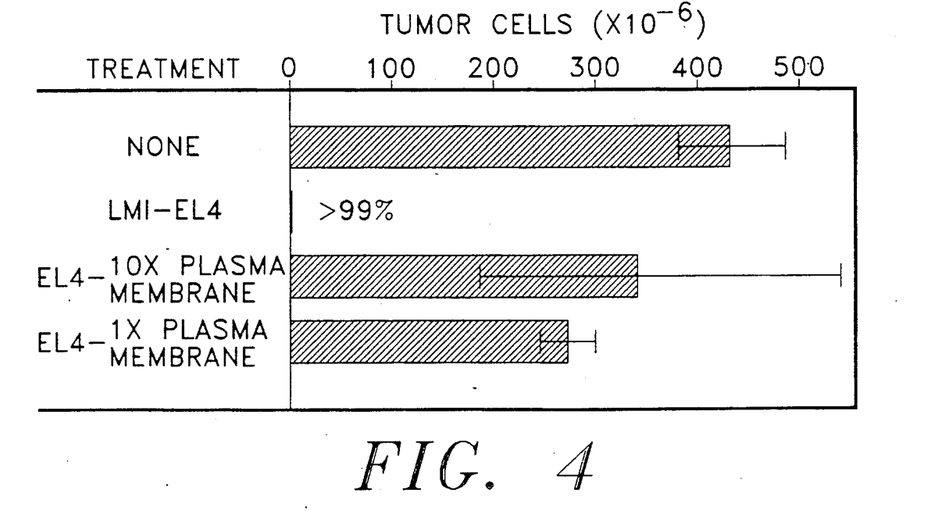
FIG. 4 graphically depicts data showing that tumor reduction requires that tumor antigen (plasma membrane) be administered on LMI, not as free plasma membrane vesicles.
Figure 5:
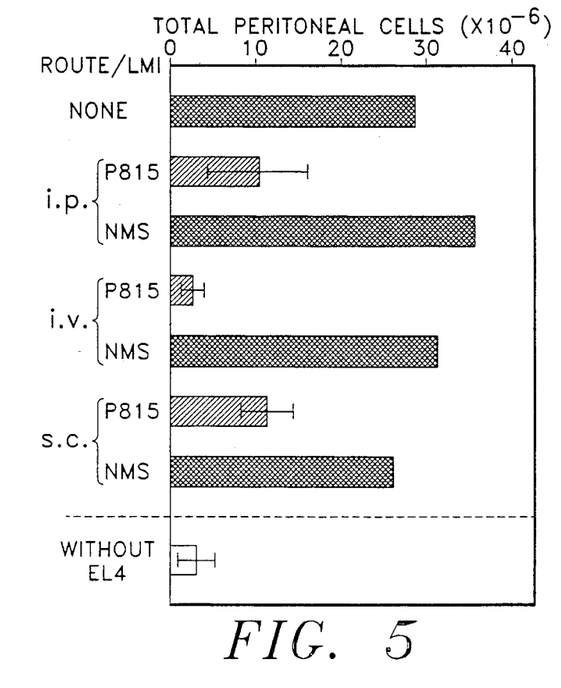
FIG. 5 graphically depicts data comparing effectiveness of three routes of LMI administration for reducing tumor growth.

Reduction of tumor load depends critically upon the physical size of the antigen-bearing particle. Administration of isolated plasma membrane vesicles, having diameters of less than $0.2\mu$, has no significant effect on tumor growth, while the same vesicles incorporated onto LMI effectively reduce (or eliminate) tumor growth (FIG. 4). In the above experiments LMI were administered intraperitoneally, i.e. at the site of tumor growth. LMI are also effective in reducing intraperitoneal tumor growth when administered subcutaneously or intravenously (FIG. 5). Current data indicate that i.v. administration may be the most effective route, but the invention is not dependent upon i.v. administration. These results expand the potential for LMI use in immunotherapy in that they demonstrate that LMI do not have to be administered at the site of tumor growth to be effective.

Figure 6A:
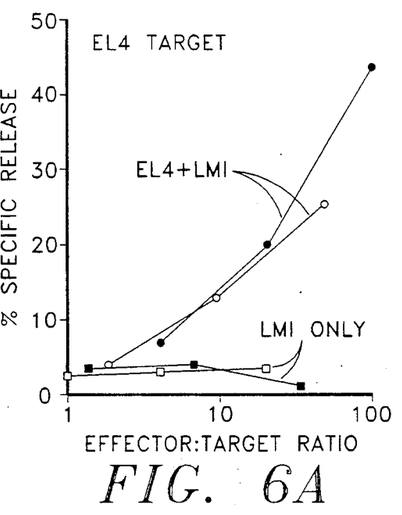
FIG. 6 graphically depicts data showing the tumor-specific cytolytic activity of peritoneal exudate lymphocytes from mice treated with LMI.
Figure 6B:
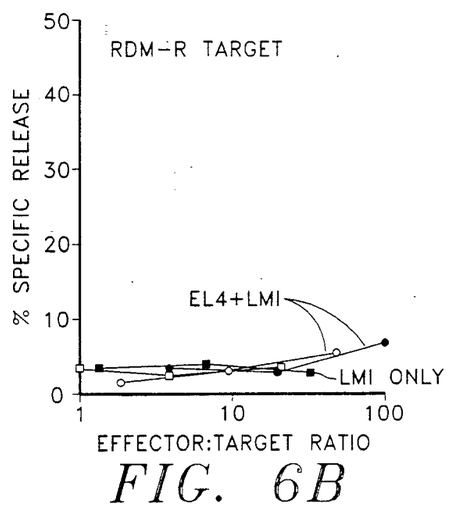
Figure 7A:
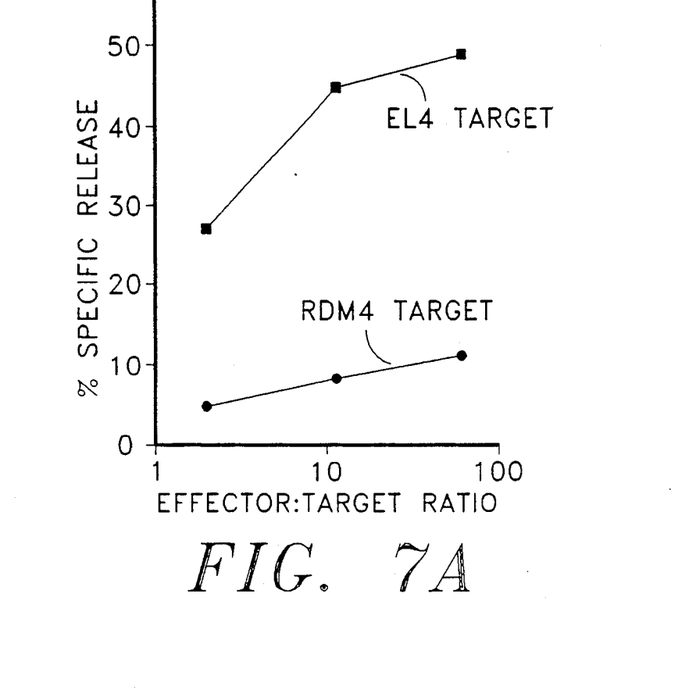
FIG. 7 graphically depicts data showing the restimulation of tumor-specific CTL response by spleen cells from LMI treated mice.
Figure 7B:
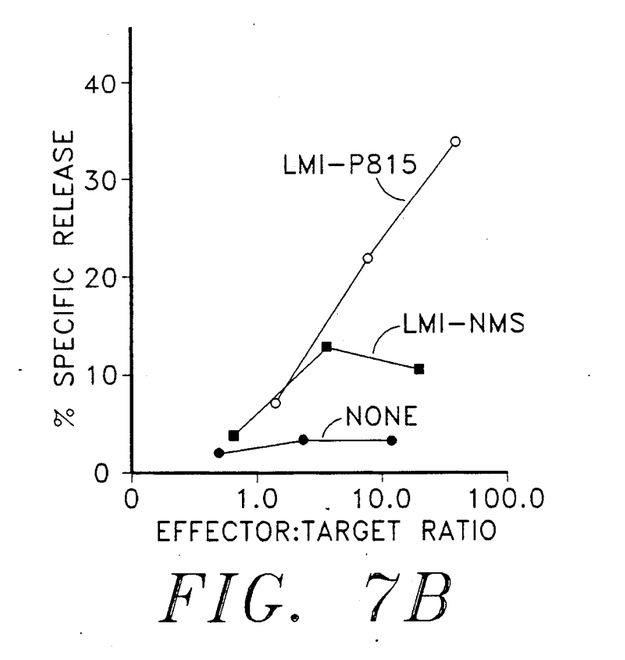

Mice make little or no tumor-specific CTL response upon inoculation with the syngeneic tumors employed here, and the tumors grow and kill the animal. In contrast, potent tumor specific cytolytic activity was found in mice inoculated with tumor and treated with LMI. Peritoneal exudate lymphocytes from tumor-inoculated, LMI-treated animals (7 to 10 days after inoculation) showed strong lytic activity against the tumor used for inoculation, but no lytic activity for an irrelevant tumor target (FIG. 6). Tumor-specific cytolytic activity in treated animals was also shown by demonstrating that spleen cells from these animals made a strong, tumor-specific response upon in vitro restimulation (FIGS. 7A and B). In contrast, spleen cells from tumor-bearing animals which did not receive LMI treatment made no response (FIG. 7B).

Thus, as in the case of the allogeneic response, antigen-bearing LMI augment (from undetectable levels) tumor specific cytolytic responses. Concomitant with activation of the lytic response is a dramatic reduction or elimination of tumor growth in the animals. While not yet proven, it appears very likely that the activated cytolytic T lymphocytes mediate the elimination of tumor growth. Irrespective of the mechanism of action of LMI treatment, the results obtained clearly indicate the value of the invention in mammalian cancer immunotherapy. Furthermore, the parallel findings obtained for the two distinct model systems studied provide strong support for the conclusion that treatment with LMI bearing the appropriate antigens will be useful in immunization and/or therapy for other diseases where T lymphocytes can have protective roles, including viral, bacterial and parasitic infections, graft-versus-host disease and autoimmune diseases.

The findings in the in vivo experiments described above have shown a close parallel between the in vitro activity of LMI in activating T cells and their in vivo activity. Based on this, further in vitro experiments have indicated a number of potentially useful approaches to construction of LMI's which would have enhanced in vivo activity. For example, LMI's bearing only nominal antigens (i.e. no MHC Class I or Class II protein) activate in vitro CTL responses. Examples of such nominal antigens include peptides corresponding to sequences present in viral proteins or in tumor-specific antigens. An appropriate viral peptide can activate serine esterase release by cloned, virus-specific CTL, and that hapten alone can stimulate cloned, hapten-specific CTL, provided that the nominal antigen is incorporated onto LMI.

LMI's bearing antigen plus additional molecules which bind to components on T cell surfaces promote specific interactions. Co-incorporation of alloantigen and additional ligands results in greater in vitro CTL response than obtained with just alloantigen on the LMI. Additional LMI ligands shown to enhance antigen-specific triggering include antibodies specific for CTL surface proteins (including H-2, theta and Lyt-2), and irrelevant Class I (but not Class II) proteins. Based on the effects obtained in vitro, these approaches will have application to design of LMI having optimal in vivo activity for eliciting particular responses.

In summary, in earlier efforts to determine whether in vivo administration of alloantigen on liposomes could stimulate or augment in vivo CTL responses, a good antibody response to the alloantigen was obtained, but no effects on generation of CTL responses were seen.

It has now been found that the same alloantigen, when incorporated onto 5μ beads to produce Large Multivalent Immunogen, can dramatically augment in vivo CTL responses to antigen-bearing cells. The therapeutic potential of this approach has been demonstrated by the findings that LMI bearing the appropriate tumor antigen dramatically reduce (or eliminate) in vivo growth of tumors in mice. Critical parameters for production of effective LMI are the particles size ($>0.2\mu$; e.g. $5\mu$ diameter) and density of antigen on the particle. Demonstration of efficacy of LMI treatment in two distinct model systems (allogeneic and tumor-specific responses) allows the conclusion that this approach provides potential benefits for immunization and/or therapy in other diseases involving T cell responses.

DETAILS OF DATA

I.p. injection of allogeneic tumor cells results, in 8 to 12 days, in a peritoneal exudate lymphocyte population having alloantigen-specific CTL activity, and optimal responses are obtained using $10^7$ stimulator cells. When $10^7$ alloantigen-bearing LMI are injected i.p. along with the stimulator cells, the cytolytic activity of PEL harvested 10 days later is dramatically augmented over that of PEL from animals injected with just stimulator cells. FIG. 1 shows results of a double reciprocal experiment demonstrating that LMI augment if they bear the same alloantigen as the stimulator cells, but do not stimulate a response when injected alone. CD2 ($H-2^d$) responders were injected i.p. with RDM4 ($H-2^k$) or EL4 ($H-2^b$) cells and LMI-bearing $H-2K^k$ or $H-2K^b$, in various combinations. $K^b$-LMI augmented generation of an EL4-specific response when administered along with EL4 stimulator cells, while $K^k$-LMI did not (left panel). $K^b$-LMI administered alone resulted in no response. The reciprocal result (right panel) was obtained using RDM4 stimulator cells. $K^k$LMI augmented when injected along with RDM4, and $K^b$LMI did not. $K^k$-LMI injected alone resulted in no response. All of the effector populations in this experiment were examined for killing of both EL4 and RDM4 targets.

As shown in FIG. 1, augmentation of in vivo CTL response is specific for the antigen on the LMI surface. CD2F1 mice were injected i.p. with the indicated stimulus. Tumor cells and beads were used at $10^7$ per animal. LMI were prepared using 10 μg H-2 protein per $10^7$ beads. $H-2K^b$ was purified from EL4 tumor cells and $H-2K^k$ from RDM4 tumor cells. 10 days after injection, peritoneal cells were removed and assayed for cytolytic activity using $^{51}$Cr-labeled RDM4 and EL4 targets in a four-hour assay at the indicated effector:target ratios. Results are shown as % specific chromium release. Cells from mice which received RDM4 stimulus (alone or with beads) did not kill EL4 targets, and cells which received EL4 stimulus (alone or with beads) did not kill RDM4 targets.

Augmented responses remained completely specific for the stimulating antigen and third party effects were not seen, i.e. effectors resulting from injection of $K^b$-LMI along with RDM4 stimulators had no lytic activity for EL4 targets.

Specificity of augmentation has been demonstrated using $H-2K^k$, $H-2K^b$ and $H-2^d$ from multiple, independent antigen and LMI preparations. Based on comparing either E:T ratio needed for a given level of target lysis, or on lytic unit determination, augmentation in these experiments has ranged from 10 to 100-fold over the response obtained when just stimulator cells were injected. As expected for CTL responses, removal of adherent cells (by one cycle of adherence to plastic) results in increased lytic activity in PEL populations from animals stimulated with just allogeneic cells and from LMI- treated animals. Effector cells present in the LMI-augmented PEL population were confirmed to be T cells by demonstration that lytic activity was eliminated if the cells were treated with anti-thyl antibody and complement prior to addition of target cells.

As pointed out, the physical form in which purified alloantigen is administered is critical. Antigen on LMI augments, but antigen incorporated into liposomes and administered at the same or higher doses has no augmenting effect. It appears that density on the LMI is also important, as it is for CTL activation in vitro. As shown in FIG. 2, specific augmentation of in vivo CTL activation depends on the antigen density on the LMI surface. C57BL/6 mice were injected i.p. with the stimulus indicated. RDM4 tumor cells and LMI were used at $10^7$ per animal. LMI bearing a high density of antigen were made using 10 μg H-2 per $10^7$ beads and low-density LMI were made using 3 μg per $10^7$. $H-2K^k$ antigen was purified from RDM4 cells and $H-2^d$ antigen from P815 tumor cells. Ten days after injection, peritoneal cells were removed and assayed for cytolytic activity using $^{51}$Cr-labeled RDM4 ($H-2^k$) and P815 ($H-2^d$) targets. PEL from 2 mice/group were pooled for assay. Greater lytic activity was found in animals treated with high density LMI than in those treated with low density LMI (FIG. 2).

Thus, alloantigen on LMI specifically augments what is otherwise an optimal in vivo response to intact allogeneic stimulators, and the resulting effector CTL retain their specificity for the stimulating alloantigen. LMI in vivo are apparently acting at the level of pCTL activation rather than on the helper arm of the response. In vitro, LMI are very effective at triggering pCTL but ineffective in providing antigen for uptake, processing and presentation to TH cells. Alloantigen on liposomes, which fails to augment in vivo, does provide antigen for in vitro TH cell activation but is very inefficient in directly activating pCTL.

LMI may stimulate expansion of the pCTL population, possibly by an IL-2 dependent autocrine mechanism. In the absence of TH cell activation (i.e. without whole cell costimulators) the proliferating precursors may fail to become effectors due to the absence of a late acting differentiation factor. Thus, LMI alone would fail to generate a lytic response (but may prime). Why LMI would stimulate pCTL expansion more effectively than intact antigen-bearing cells is not known. This might, for example, result from their interaction with pCTL for more prolonged times and thus provide for a sustained stimulation of IL-2 production.

Based on the results obtained in examining LMI effects on allogeneic CTL generation, experiments were initiated to examine the effects of antigen-bearing LMI on syngeneic tumor-specific responses. We have examined EL4, a thymoma of C57BL/6 origin, RDM4, a lymphoma of AKR origin, and P815, a mastocytoma of DBA/2 origin. All of these grow in the peritoneums of syngeneic mice and ultimately kill the host. Tumor antigen(s) relevant to CTL recognition are not defined. However, plasma membrances can be isolated from the tumor cells and presumably bear the same array of surface proteins as the intact tumor cells. That this includes antigens recognized by tumor-specific CTL is indicated by studies demonstrating that membranes isolated form tumor cells can specifically stimulate induction of secondary in vitro tumor-specific responses.

LMI-bearing tumor antigen in the form of membranes can be readily prepared by a simple dilution of beads (suspended in DMSO) into a suspension of purified plasma membrane vesicles in PBS. When antigen-bearing LMI were injected i.p. along with tumor cells into syngeneic mice, a dramatic reduction in the tumor load present by days 9 to 11 was found. This was the case for all three tumors examined, and reduction in tumor burden occurred over a tumor inoculum range of $10^5$ to $10^7$ cells (FIG. 3). Although still substantial, reduction was least in the case of RDM4, and at an inoculum level of $10^7$ RDM4 LMI treatment had little or no effect. RDM4 is the fastest growing of the three tumors examined. Tumor reduction does not occur if LMI do not bear the tumor plasma membrane. LMI coated with normal mouse serum protein have not effect on tumor load for any of the tumors examined (not shown).

As for augmenting allogeneic responses, the physical form of the antigen is critical for effective reduction of tumor load. Injection of plasma membranes as free membrane vesicles (diameter $<0.2\mu$) in suspension has little or no effect on tumor load, while the same membranes on LMI are very effective. As shown in FIG. 4, tumor reduction requires that tumor antigen (plasma membrane) be administered on LMI, not as free plasma membrane vesicles. C57BL/6 mice were inoculated i.p. with $10^6$ live EL4 cells. Administered at the same time were $10^7$ LMI-bearing EL4 plasma membrane, or EL4 plasma membrane in suspension. Membranes were used at an amount equivalent to that on the LMI ($1\times$ plasma membrane) or at a 10-fold higher dose ($10\times$ plasma membrane). Peritoneal cells were harvested and counted on day 13. Values are averages obtained for two mice in each group and the range obtained for the pair is shown.

The experiment shown in FIG. 4 examined two mice/group and the range found is shown. Most of the preliminary experiments described here have used two mice/group with the range of values being similar to those shown in FIG. 4. The data are considered adequate to demonstrate the dramatic effects of LMI treatment described here.

The limited dose response information obtained thus far indicates that LMI remain effective in reducing tumor load down to at least $10^6$/mouse (not shown), a ten-fold lower dose than in the experiments shown here. The kinetics of P815 tumor growth and LMI effects have been examined in one experiment. Mice were inoculated with $10^5$ tumor cells, with or without co-administration of LMI. By day 5, tumor growth had occurred in both control and treated animals and about $20\times10^6$ peritoneal cells/mouse were recovered. Beyond this time, growth continued in control animals, but the tumor load decreased in the treated animals. By day 9, controls had $161\times10^6$ cells/mouse while treated animals had $1.4\times10^6$.

In some experiments, the single injection of antigen-bearing LMI has resulted in a greater than 99% reduction in the number of peritoneal cells recovered compared to controls (FIG. 4 and the kinetics experiment described above). At this level, the number of cells recovered from treated animals is not significantly different from that recovered from normal animals which have not received tumor.

The effective routes of LMI administration were examined to a degree sufficient to establish effective administration routes. Mice were inoculated i.p. with $10^5$ P815 and LMI administered either i.p., i.v. (tail vein) or subcutaneously. Eleven days later the animals were sacrificed, peritoneal cells washed out and cells counted. LMI-bearing P815 membrane antigen reduced the tumor load by 60 to 70% when administered i.p. or subcutaneously. Relevant data are depicted graphically in FIG. 5. CD2F1 mice were inoculated i.p. with $10^5$ P815 cells. At the same time, LMI having either P815 plasma membrane or normal mouse serum protein (NMS) were administered by the indicated route, using $10^7$ LMI/mouse in all cases. Peritoneal cells were harvested and counted eleven days after inoculation. Groups treated with tumor-antigen bearing LMI consisted of four mice each and values shown are averages with standard deviations indicated. Control groups (tumor only and NMS-LMI treated) were of two mice each and averages are shown. Recovery of peritoneal washout cells from normal mice which received neither tumor inoculum or LMI was determined for six mice (bottom bar), and the standard deviation is indicated.

I.v. administration was even more effective than i.p. or s.c. administration, and the number of cells recovered from these mice was no greater than the number recovered from normal mice which received no tumor inoculum. For all routes of administration, control LMI coated with normal mouse serum protein caused no significant reduction in tumor load. Current data indicate that i.v. administration may be the most effective route, but the invention is not dependent upon i.v. administration. These results also expand the potential for LMI use in immunotherapy, in that they demonstrate that LMI do not have to be administered at the site of tumor growth to be effective.

Given the effects of antigen-bearing LMI on allogeneic CTL responses, LMI administration is considered to effect in vivo tumor as a result of activation of tumor-specific CTL responses. When non-adherent PEL cells from mice injected with EL4 tumor cells and LMI-bearing EL4 plasma membrane were tested in a 4 hr $^{51}$Cr release assay, cytolytic activity for EL4 targets was present, as shown in FIG. 6. The data in FIG. 6 illustrate the tumor-specific cytolytic activity of peritoneal exudate lymphocytes from mice treated with LMI. C57BL/6 mice were inoculated with $10^6$ live EL4 cells. Treated mice received $10^7$ LMI bearing EL4 membrane at the same time (EL4+LMI). Control mice without live tumor were also injected with $10^7$ LMI bearing EL4 membrane (LMI only). After 12 days, peritoneal cells were harvested, allowed to adhere to plastic for one hour and the non-adherent cells assayed for lytic activity in a 4 hr Cr-release assay using EL4 and RDM4 targets. LMI-treated mice were the same as those shown in FIG. 4 where the tumor load had been reduced >99% by LMI treatment. Cells from individual mice were assayed and results shown for both animals in each group. Killing is expressed as % specific release. Spontaneous release was 195 cpm for EL4 and 248 cpm and total releasable was 2549 for EL4 and 2938 for RDM4.

The data indicate that the activity was specific in that no activity was detected on RDM4 targets. PEL from mice injected with LMI, but no live tumor cells, showed no lytic activity on either target. PEL from mice injected with tumor, but not treated with LMI also had no killing activity (not shown), but the large number of tumor cells present in this population precludes definitive interpretation as they could act as cold target blockers.

Tumor-bearing animals were compared with LMI-treated animals for cytolytic activity in spleen cell populations following in vitro restimulation with irradiated tumor cells in 6-day cultures to further examine lytic responses. These data are depicted in FIG. 7. FIG. 7A depicts the specificity of CTL from restimulated spleen cells of LMI treated EL4-tumor-bearing C57BL/6 mice and FIG. 7B depicts the effect of treatment on restimulation of spleen cells from P815-tumor-bearing CD2F1 mice.

C57BL/6 mice were inoculated i.p. with $10^6$ live EL4 cells and $10^7$ LMI bearing EL4 antigen administered at the same time (FIG. 7A). Twelve days later spleens (2 mice) were removed, pooled and placed into culture with or without irradiated EL4 cells. After 6 days of in vitro culture, cells were assayed for lytic activity in a 4 hr Cr-release assay using EL4 and RDM4 targets. Results are shown for cells cultured with irradiated EL4. Cells cultured in the absence of stimulators had no lytic activity on either target.

CD2F1 mice were inoculated with $10^6$ live P815 cells and treated at the same time with either nothing (None), $10^7$ LMI bearing P815 antigen (LMI-P815), or $10^7$ LMI bearing normal mouse serum (LMI-NMS) (FIG. 7B). Seven days later, spleens were removed (2 mice per group) and placed into culture alone or with irradiated P815 cells. After 6 days of in vitro culture, lytic activity was assayed on P815 and RDM4 targets. Results obtained for restimulated cells on P815 targets are shown. No killing of RDM4 targets was found. Cells which were not restimulated in vitro lysed neither P815 nor RDM4 targets.

FIG. 7A shows that spleen cells taken 12 days after mice were injected with EL4 tumor and LMI could generate a strong cytolytic response against EL4 targets, but not RDM4 targets. This response occurred only in cultures where irradiated EL4 stimulators were added. Similar results were obtained when spleen cells were examined from mice injected with P815 tumor cells and either no other addition, antigen-bearing LMI, or LMI coated with normal mouse serum. Restimulation with irradiated P815 resulted in generation of a strong anti-P815 response from mice that had been treated with tumor and antigen-bearing LMI (FIG. 7B). In contrast, little or no response was obtained from the cells of mice which received only tumor, or tumor and normal mouse serum coated LMI. In all cases, no response was obtained in the absence of irradiated P815 stimulator cells.

Essentially identical results were obtained in the same kind of experiment examining RDM4 tumor in AKR mice. Spleen cells taken from mice 12 days after injection with RDM4 and antigen-bearing LMI generated a strong response (61% lysis at an E:T of 2:1) that depended on restimulation with irradiated stimulators and was specific for RDM4 targets. Cells from mice given only tumor generated little response upon restimulation (8% at 2:1) as did spleen cells from normal mice which received neither tumor cells nor LMI. Thus, LMI treatments which result in PEL activity, or activity upon in vitro restimulation, also result in reduced peritoneal tumor load in comparison to controls.

SUMMARY

Thus, LMI treatment of tumor-bearing animals results in both dramatic reduction in tumor load and appearance of potent tumor specific cytolytic activity. The magnitude and specificity of the lytic activity, and the antigen-dependent restimulation of a response by spleen cells, all argue very strongly that this is mediated by cytolytic T lymphocytes. Irrespective of the mechanism of action of LMI treatment, the results obtained thus far indicate the value of the invention in mammalian cancer immunotherapy.

Therapeutic uses for LMI include in vivo administration alone, or in combination with other agents, to immunize against disease or as therapy for ongoing diseases. Diseases where LMI will prove efficacious include viral, bacterial and parasitic diseases, cancer, graft-versus-host disease, and autoimmune diseases. Ligands used on LMI include, but are not limited to, MHC molecules, natural or synthetic peptide antigens, protein antigens, isolated plasma membranes, antibodies and other ligands bound by cell surface components.

While considerable work remains before a complete characterization of the mechanism(s) by which LMI augment in vivo generation of CTL responses will be possible, and it is not yet known whether the cytolytic response mediates the dramatic reduction of elimination of a tumor which is well developed before LMI immunotherapy is commenced, the data and results presented signal a major breakthrough in the treatment and prevention of disease.

INDUSTRIAL APPLICATION

This invention finds application in research and in immunization and/or immunotherapy for tumors and other cell-mediated diseases of mammals, e.g. in veterinary medicine, and in immunotherapeutic treatment of human cancer.

I claim:

1. A method of treating a mammal having a tumor to activate cell responses comprising the in vivo administration of large multivalent immunogen consisting essentially of multivalent ligand arrays supported on beads having a major diameter of about 5 microns.

2. The method of claim 1 further comprising the step of administering a chemotherapeutic agent substantially contemporaneously with the administration of the large multivalent immunogen.

3. The method of claim 1 further comprising the step of administering the chemotherapeutic agent cyclophosphamide substantially contemporaneously with the administration of the large multivalent immunogen.

4. The method of claim 1 further comprising the substantially contemporaneous administration of a lymphokine or antigen incorporate into a liposome or a mixture of lymphokine incorporated into a liposome and antigen incorporated into a liposome.

5. The method of claim 4 further comprising the step of administering a chemotherapeutic agent substantially contemporaneously with the administration of the large multivalent immunogen.

6. The method of claim 4 further comprising the step of administering the chemotherapeutic agent cyclophosphamide substantially contemporaneously with the administration of the large multivalent immunogen.

7. A method of treating a mammal having a tumor to activate antigen-specific T cell comprising the in vivo administration of large multivalent immunogen consisting essentially of multivalent ligand arrays supported on beads having a major diameter of about 5 microns.

8. The method of claim 7 further comprising the step of administering a chemotherapeutic agent substantially contemporaneously with the administration of the large multivalent immunogen.

9. The method of claim 7 further comprising the step of administering the chemotherapeutic agent cyclophosphamide substantially contemporaneously with the administration of the large multivalent immunogen.

10. The method of claim 7 further comprising the substantially contemporaneous administration of a lymphokine or antigen incorporate into a liposome or a mixture of lymphokine incorporated into a liposome and antigen incorporated into a liposome.

11. The method of claim 10 further comprising the step of administering a chemotherapeutic agent substantially contemporaneously with the administration of the large multivalent immunogen.

12. The method of claim 10 further comprising the step of administering the chemotherapeutic agent cyclophosphamide substantially contemporaneously with the administration of the large multivalent immunogen.

13. A method of treating a mammal having a tumor to activate macrophages, monocytes or natural killer cells comprising the in vivo administration of large multivalent immunogen consisting essentially of multivalent ligand arrays supported on beads having a major diameter of about 5 microns.

14. The method of claim 13 further comprising the step of administering a chemotherapeutic agent substantially contemporaneously with the administration of the large multivalent immunogen.

15. The method of claim 13 further comprising the step of administering the chemotherapeutic agent cyclophosphamide substantially contemporaneously with the administration of the large multivalent immunogen.

16. The method of claim 13 further comprising the substantially contemporaneous administration of a lymphokine or antigen incorporate into a liposome or a mixture of lymphokine incorporated into a liposome and antigen incorporated into a liposome.

17. The method of claim 16 further comprising the step of administering a chemotherapeutic agent substantially contemporaneously with the administration of the large multivalent immunogen.

18. The method of claim 16 further comprising the step of administering the chemotherapeutic agent cyclophosphamide substantially contemporaneously with the administration of the large multivalent immunogen.

* * * * *